United States Patent [19]

Haendle

[11] Patent Number: 4,807,273

[45] Date of Patent: Feb. 21, 1989

[54] VOICE CONTROLLED X-RAY DIAGNOSTICS INSTALLATION

[76] Inventor: Joerg Haendle, Leipziger Str. 16g, D8520 Erlangen, Fed. Rep. of Germany

[21] Appl. No.: 105,005

[22] Filed: Oct. 6, 1987

[30] Foreign Application Priority Data

Oct. 28, 1986 [DE] Fed. Rep. of Germany ....... 3636678

[51] Int. Cl.⁴ .............................................. H05G 1/02
[52] U.S. Cl. ..................................... 378/197; 378/98; 378/116
[58] Field of Search ...................... 378/99, 98, 62, 197, 378/116

[56] References Cited

U.S. PATENT DOCUMENTS

| | | |
|---|---|---|
| 4,101,774 | 7/1978 | Elzinga et al. . |
| 4,200,798 | 4/1980 | Neuendorf et al. ............... 378/98 |
| 4,207,959 | 6/1980 | Yordin et al. . |
| 4,247,777 | 1/1981 | Pfeifer et al. .................... 378/98 |
| 4,553,254 | 11/1985 | Bach et al. ....................... 378/98 |
| 4,599,739 | 7/1986 | Nishikawa ....................... 378/98 |
| 4,680,628 | 7/1987 | Wajcik et al. .................... 378/99 |

FOREIGN PATENT DOCUMENTS

| | | |
|---|---|---|
| 0077194 | 4/1983 | European Pat. Off. . |
| 0220501 | 5/1987 | European Pat. Off. . |
| 3031507 | 2/1982 | Fed. Rep. of Germany . |
| 3218301 | 11/1983 | Fed. Rep. of Germany . |
| 3532730 | 3/1987 | Fed. Rep. of Germany . |
| 1439547 | 6/1976 | United Kingdom . |

*Primary Examiner*—Carolyn E. Fields
*Assistant Examiner*—David P. Porta

[57] ABSTRACT

An x-ray diagnostics installation has motor-actuatable adjustable supports for various components which are operated by signals from a central control computer to selectively position the components with respect to an examination subject. The central control computer has an input connected to a microphone through a voice processor so that voice commands can be used to initiate and stop positioning of the components in various directions. The central control computer is also connected to a display through a graphics processor, so that the relative positions of all of the components and the examination subject can be visually presented.

9 Claims, 2 Drawing Sheets

VOICE CONTROLLED X-RAY DIAGNOSTICS INSTALLATION

BACKGROUND OF THE INVENTION

1. Field of the Invention

The present invention is directed to an x-ray diagnostics installation having motor-actuatable adjustment means for positioning the components of the apparatus, and a control unit for the adjustment means with a command input for entering positioning commands.

2. Description of the Prior Art

An x-ray diagnostics installation is disclosed in German OS No. 32 18 301 having a feedback loop control mechanism for adjusting the position of the x-ray tube and the radiation receiver. Two columns are displaceably attached to a carrier secured to the ceiling of the examination room, and an x-ray tube and an x-ray image intensifier are mounted at the respective free ends of these columns. The length of the columns can be varied, so that the height of the x-ray tube and the x-ray image intensifier can be adjusted. The x-ray tube and the image intensifier can also be pivoted around the column axis. The feedback control loop electrically couples the adjustment drives for both components so that the imaging system is always aligned with the x-ray tube such that the x-ray beam is incident on a radiation-sensitive surface of the image intensifier.

In such a system, the means for entering positioning data into the system are generally a control counsel or a remote control unit. Operating the installation becomes increasing difficult given a plurality of controllable components and given the possibility of being able to freely select the position of these components. As the number of adjustable components increases, with each component requiring its own acutation element on the control panel, the control panel becomes too congested and complex to permit quick use by the technician or physician.

SUMMARY OF THE INVENTION

An object of the present invention is to provide an x-ray diagnostics installation having a plurality of positionadjustable components wherein commands for positioning the components can be entered in a simple manner and with continuous supervision by the operator.

The above object is achieved in accordance with the principles of the present invention in an x-ray diagnostics installation wherein the entry of positioning commands is accomplished by a microphone and a voice processor which analyzes the voice commands from the microphone. The noice processor is connected to a central control computer, which in turn controls the drive of the motors for positioning the various components, and also controls a graphics processor. The graphics processor is connected to the input of a diaply for visually presenting the current positions of the respective components. Using this apparatus, it is possible to undertake a pre-adjustment of the apparatus components using a voice command and monitoring the component positions on the display. When an optimum setting reproduced on the display has been reached, and after conclusion of a current examination, the components of the installation can then assume the optimum position shown on the display for a subsequent examination of the same patient.

A high degree of mobility of the apparatus components is achieved using a plurality of robot arms for respectively supporting the various components. Each robot arm comprises a first lever attached to a retaining point in a rotatable and pivotable manner, the first lever having a free end pivotably connected to a second lever which has an opposite end on which the component is mounted. One such arm may be provided, for example, for the x-ray tube and another such arm for the x-ray imaging system.

The control instructions recognized by the voice processor can be directly supervised by connecting a circuit for voice output to the voice processor. The voice output circuit repeats the command, as analyzed by the voice processor, and plays the command back through a speaker for verification.

A control computer for the imaging electrons may be connected to the central control computer so that the central control computer can operated the graphics processor based on the voice input with symbols for the individual system components of the video system being represented on the display.

DESCRIPTION OF THE PREFERRED EMBODIMENTS

Figure 1:
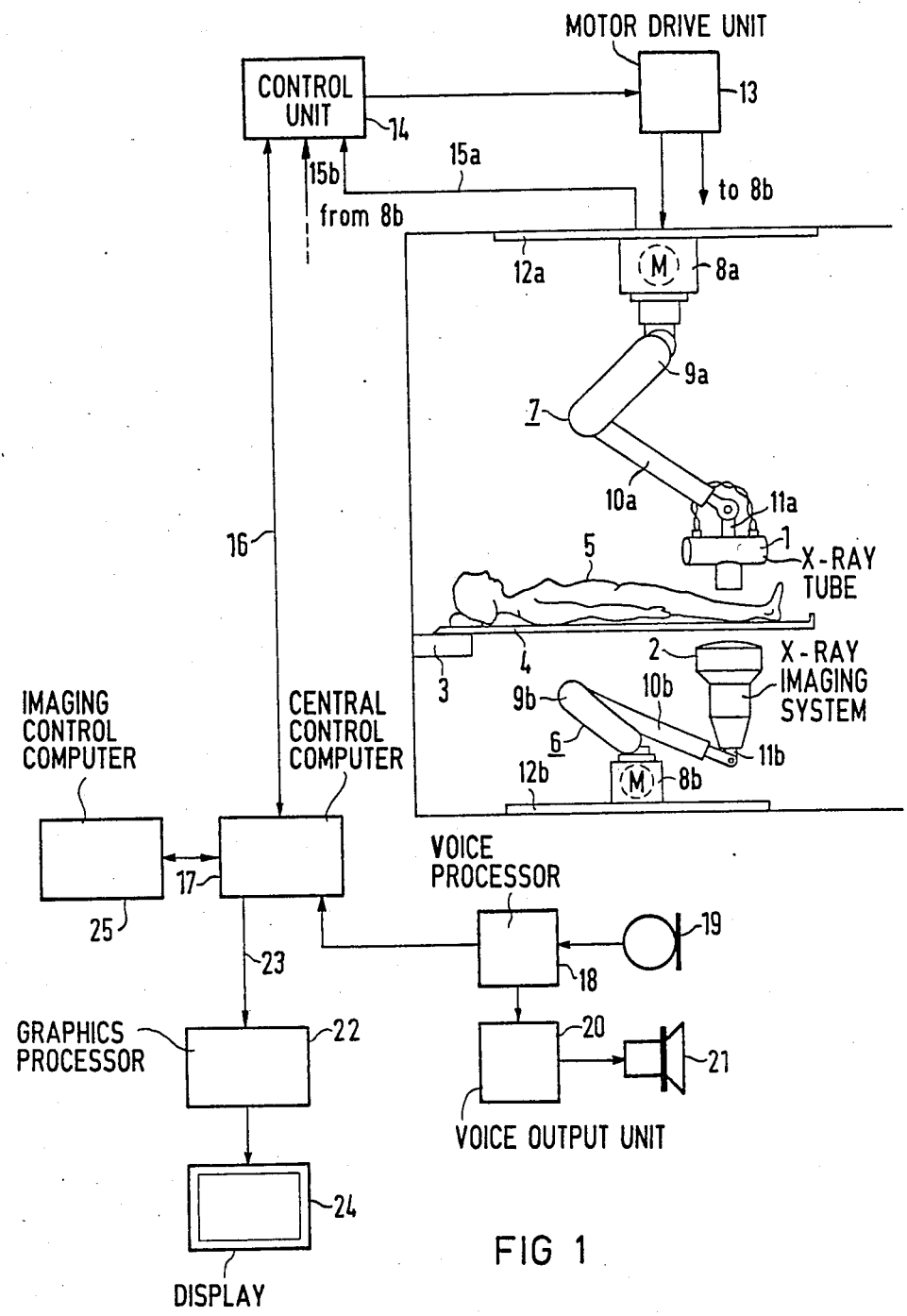
FIG. 1 is a schematic block diagram of an x-ray diagnostics installation constructed in accordance with the principles of the present invention.

An x-ray diagnostics installation constructed in accordance with the principles of the present invention is shown in an examination room in FIG. 1. The installation includes an x-ray tube 1, an x-ray imaging system 2, having an x-ray image intensifier and a connected video camera, and a patient support 4 attached to a wall of the examination room by a moveable mount 3 and having an examination subject 5 thereon. The x-ray tube 1 and the x-ray imaging system 2 are held by respective supports 6 and 7, which may be robot arms. The support 7 is connected to a pedestal 8a displaceably mounted on rails 12a attached to the ceiling of the examination room. The support 6 is attached to a pedestal 8b mounted on rails 12b attached to the floor of the examination room. The support 6 consists of a first lever 9b having one end connected to the pedestal 8b and a free end connected to a second lever 10b. The free end of the lever 10b has a mount 11b thereon, to which the x-ray imaging system 2 is attached. The support 7 has a first lever 9a having one end connected to the pedestal 8a and a free end connected to a second lever 10a. The free end of the lever 10a is connected to a mount 11a, to which the x-ray tube 1 is attached. Each of the supports 6 and 7 in the form of robot arms are motor-actuated by respective motors N, schematically shown in the pedestals 8a and 8b.

Each of the motors for the supports 6 and 7 are operated by a motor drive unit 13 which is controlled by a control unit 14. Coordinate values from suitable sensors arranged in the brackets 6 and 7 in a known manner are supplied to the control unit 14 on lines 15a and 15b from which the current position of each component of the installation can be identified. The control unit 14 is connected to a central control computer 17 via a line 16. A microphone 19 is also present in the examination room, having an output connected to a voice processor 18. The output of the voice processor 18 is supplied to the central control computer 17 and to a voice output unit 20. The voice output unit 20 is connected to a speaker 21 for re-playing the entered voice command for verification.

Figure 2:
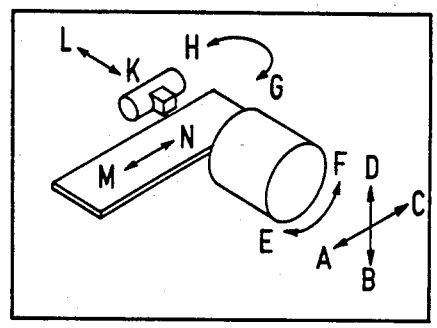
FIG. 2 is an example of a display presentation of the apparatus components and the control instructions therefore.

The control computer 17 is also connected to a graphics 22 via a line 23. The graphics processor 22 generates signals for a three-dimensional display of the apparatus components on a display 24, for example, a plasma display. Such a three-dimensional display is a pseudo-3D illustration with oblique projection and shadowing as shown, for example, in FIG. 2. The display 24 receives the coordinate values from the control unit 14 via the central control computer 17 and displays the spatial positions of the components such as the x-ray tube 1, the imaging system 2 and the patient support 4 relative to each other by means of the signals generated by the graphics processor 22. Arrows identified with letters A through N indicate the possible movements of the apparatus components and are indicated in the three-dimensional display. By voice input of these letters A through N via the microphone 19, the voice processor 18 analyzes the command and generates a control instruction. This control instruction is converted back into a voice signal via the circuit 20 for output through the speaker 21 for verification. The control instruction is also supplied to the central control computer 17, which simulates a modification of the positions of the components in response thereto, as if such movements were actually being made and were being displayed on the basis of the coordinate signals. The simulated movement of the apparatus components 1 through 4 is portrayed on the display 24. By entering a stop command (by voice) the continuous modification of the position of the apparatus components is arrested. The new position of the components 1 through 4 can thereby be pre-set and checked by observing the display 24, before entering an instruction which activates actual movement of the apparatus components.

Figure 3:
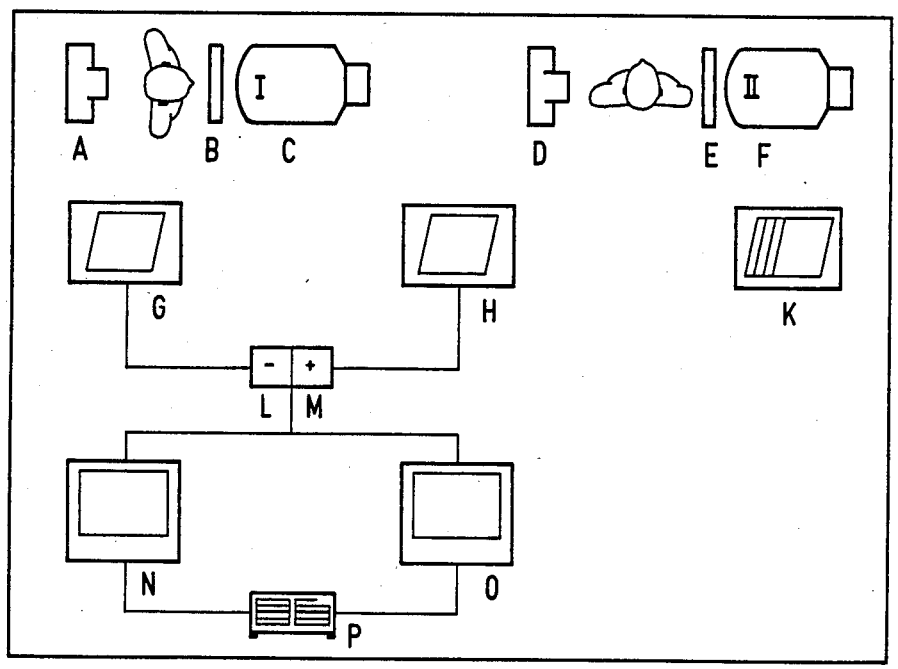
FIG. 3 is an example of a display presentation of the system components of the video system with the control instructions therefore.

The control computer 17 may also be connected to an imaging control computer 25 for the image electronics. For control of the system components of the video system, the representation on the display 24 is changed by a voice command through the microphone 19 and the voice processor 18 so that the illustration shown in FIG. 3 appears on the display 24. By entering a voice command such as the letters A through P, the corresponding components of the video system can be switched on. For example, the x-ray tube of a first x-ray diagnostics installation I can be achieved by the voice command A. The voice command B selects the direct exposure. The voice command C switches the x-ray image intensifier on. A second x-ray diagnostics installation II can also be provided, with corresponding commands D, E and F controlling that system. By entering voice commands G, H or K, individual memories, or a combination of such memories, can be activated. Subtraction of the image information contained in the image memories can be undertaken by voice command L, or an addition or integration of that data can be undertaken by the voice command M. The image signals processed in this fashion can be presented on monitors N or O on the bases of a voice command. A hard copy generator can be switched on by the voice command P. On the basis of a corresponding combination of the voice commands, thus a transillumination, a series image storing, digitial subtraction angiography, exposures using the path-finder technique, stereo technique, and subsequent subtraction can be undertaken.

The x-ray diagnostics installation disclosed herein permits adjustment of the apparatus and video components to be undertaken in a simple manner while the operator simultaneously supervises the adjustment on the display. A large number of confusingly arranged adjustment controls are not needed by virtue of all control instructions being entered by voice commands, so that the operation of the installation is considerable simplified. The installation also provides the possibility of pre-adjusting certain apparatus positions and interconnections of the system components.

Although modifications and changes may be suggested by those skilled in the art it is the intention of the inventor to embody within the patent warranted hereon all changes and modifications as reasonably and properly come within the scope of his contribution to the art.

I claim as my invention:

1. An x-ray diagnostics installation for examining a subject comprising:
   a plurality of diagnostic components;
   a like plurality of adjustable means for respectively supporting and positioning said diagnostic components with respect to said subject;
   control means for operating said adjustable means to selectively position said components;
   computer means for generating signals for operating said control means;
   graphics processor means connected to said computer means for generating signals corresponding to a pictorial simulation of said components and their positions with respect to said subject;
   display means connected to said graphics processor means for visually presenting said pictorial simulation of said components and their positions with respect to said subject; and
   means for providing input commands to said computer means for selectively positioning said components by voice.

2. An x-ray diagnostics installation as claimed in claim 1, wherein said control means includes a drive means and wherein each adjustable means is a robot arm comprising:
   a first lever having first and second ends;
   means for pivotably and rotatably connecting said first end of said first lever to said drive means;
   a second lever having first and second ends, said first end of said second lever being pivotably connected to said second end of said first lever; and
   means for pivotably and rotatably connecting one of said diagnostic components to said second end of said second lever.

3. An x-ray diagnostics installation as claimed in claim 1, further comprising means for playing back and audibly repeating the voice input commands.

4. An x-ray diagnostics installation as claimed in claim 1, further comprising a video system of which said display means is a component, said video system having a plurality of other video system components, and an imaging control means connected to said computer means, and a graphics processor means connected between said computer means and said display means for selectively generating signals for presenting either said simulation of said diagnostic components or a simulation of said video system components, said imaging control means being responsive to a voice input command supplied to said imaging control means through said computer means to switch said graphics processor means through said computer means to cause said display means to present either said simulation of said diagnostic components or said simulation of said video system components.

5. An x-ray diagnostics installation as claimed in claim 1, wherein said means for providing input commands by voice comprises a microphone and a voice processor connected between said microphone and said computer means.

6. An x-ray diagnostics installation as claimed in claim 1, wherein said control means comprises:
   a motor for each of said adjustable means;
   a motor drive unit connected to each motor; and
   a control unit connected to said motor drive unit and said computer means, said control unit providing the motors to operate said adjustable means selectively position said components and receiving signals from said motors corresponding to the respective positions of said components, said control unit providing signals corresponding to said signals from said motors to said computer means.

7. An x-ray diagnostics installation for examining a subject comprising:
   a plurality of diagnostic components;
   a like plurality of motor-operated adjustable means for respectively positioning said diagnostic components with respect to said subject;
   a microphone;
   a voice processor having an input connected to said microphone;
   a control computer having an input connected to an output of said voice processor and an output connected to said motor-operated adjustable means to operate said adjustable means to selectively position said components; and
   graphics display means connected to a further output of said control computer for pictorially presenting a simulation of said diagnostic components and their positions with respect to said subject.

8. An x-ray diagnostics installation for examining a subject comprising:
   an x-ray tube which directs a beam of x-radiation at said subject;
   a first motor-driven adjustable robot arm connected to said x-ray tube for supporting and positioning said x-ray tube with respect to said subject;
   an x-ray imaging system which receives x-radiation from said x-ray tube attenuated by said subject;
   a second motor-driven adjustable robot arm connected to said x-ray imaging system for supporting and positioning said x-ray system with respect to said subject;
   control means for operating each of said robot arms to selectively respectively position said x-ray tube and said x-ray imaging system with respect to said subject;
   computer means connected to said control means for providing signals to said control means for operating said robot arms;
   graphics processor means connected to said computer means for generating signals corresponding to pictorial simulations of at least said x-ray tube, said subject and said x-ray imaging system and their positions relative to each other;
   display means connected to said graphics processor means for visually presenting the pictorial simulation of at least said x-ray tube, said subject and said x-ray imaging system and their positions with respect to each other in response to signals from said computer means; and
   means connected to said computer means for converting selected voice commands into signals usable by said computer means for operating said control means and said display means.

9. An x-ray diagnostics installation as claimed in claim 8, wherein said graphics processor means includes means for generating a selected different simulation, and said x-ray diagnostics installation further comprising:
   imaging control means connected to said computer means and responsive to a voice command through said computer means for switching said graphics processor means for presenting either said pictorial simulation or said further different simulation on said display means.

* * * * *